US012303581B2

(12) United States Patent
Lorant et al.

(10) Patent No.: US 12,303,581 B2
(45) Date of Patent: May 20, 2025

(54) COSMETIC EMULSION CONTAINING A GEMINI SURFACTANT AND A LIPOPHILIC POLYMER

(71) Applicant: L'OREAL, Paris (FR)

(72) Inventors: Raluca Lorant, Chevilly la Rue (FR); Laure Fageon, Chevilly la Rue (FR); Carole Guiramand, Chevilly la Rue (FR); Karl Boutelet, Chevilly la Rue (FR)

(73) Assignee: L'OREAL, Paris (FR)

( * ) Notice: Subject to any disclaimer, the term of this patent is extended or adjusted under 35 U.S.C. 154(b) by 176 days.

(21) Appl. No.: 16/760,191

(22) PCT Filed: Nov. 15, 2018

(86) PCT No.: PCT/EP2018/081467
§ 371 (c)(1),
(2) Date: Apr. 29, 2020

(87) PCT Pub. No.: WO2019/096953
PCT Pub. Date: May 23, 2019

(65) Prior Publication Data
US 2021/0177719 A1 Jun. 17, 2021

(30) Foreign Application Priority Data
Nov. 15, 2017 (FR) ........................... 1760735

(51) Int. Cl.
| | | |
|---|---|---|
| A61K 8/44 | (2006.01) | |
| A61K 8/06 | (2006.01) | |
| A61K 8/42 | (2006.01) | |
| A61K 8/45 | (2006.01) | |
| A61K 8/46 | (2006.01) | |
| A61K 8/81 | (2006.01) | |
| A61K 8/86 | (2006.01) | |
| A61Q 1/14 | (2006.01) | |
| A61Q 17/04 | (2006.01) | |
| A61Q 19/10 | (2006.01) | |

(52) U.S. Cl.
CPC ............... *A61K 8/44* (2013.01); *A61K 8/06* (2013.01); *A61K 8/062* (2013.01); *A61K 8/42* (2013.01); *A61K 8/45* (2013.01); *A61K 8/463* (2013.01); *A61K 8/466* (2013.01); *A61K 8/8152* (2013.01); *A61K 8/86* (2013.01); *A61Q 1/14* (2013.01); *A61Q 17/04* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,128,634 A | 12/1978 | Hase et al. | |
| 4,128,635 A | 12/1978 | Hase et al. | |
| 2004/0005279 A1 | 1/2004 | Lorant et al. | |
| 2007/0264204 A1 | 11/2007 | Noor et al. | |
| 2009/0105353 A1* | 4/2009 | Lorant | A61P 17/00 514/772.3 |
| 2010/0202985 A1 | 8/2010 | Sengupta | |
| 2011/0097288 A1 | 4/2011 | Janssen | |
| 2012/0244202 A1 | 9/2012 | Simonnet | |
| 2013/0052148 A1 | 2/2013 | Chavan | |
| 2016/0250137 A1* | 9/2016 | Noor | A61K 8/891 424/60 |
| 2017/0348219 A1 | 12/2017 | Uyama | |

FOREIGN PATENT DOCUMENTS

| | | |
|---|---|---|
| CN | 101442979 A | 5/2009 |
| CN | 102762186 A | 10/2012 |
| CN | 104936575 A | 9/2015 |
| CN | 107250181 A | 10/2017 |
| DE | 26 08 875 A1 | 9/1977 |
| DE | 2608834 A1 | 9/1977 |
| EP | 1 386 600 A1 | 2/2004 |
| EP | 2 039 339 A2 | 3/2009 |
| EP | 3 235 839 A1 | 10/2017 |
| FR | 2 843 020 A1 | 2/2004 |
| FR | 2921262 A1 | 3/2009 |
| FR | 3 046 076 A1 | 6/2017 |
| GB | 1 560 428 A | 2/1980 |
| JP | 52 108030 A | 9/1977 |
| JP | 2009 120493 A | 6/2009 |
| JP | 2009 536949 A | 10/2009 |
| JP | 2012144580 A | 8/2012 |
| JP | A-2012-144580 A | 8/2012 |
| JP | 2013-520464 A | 6/2013 |

(Continued)

OTHER PUBLICATIONS

JPO English abstract for JP 2015-131767 (Sase et al) (Year: 2015).*

(Continued)

*Primary Examiner* — Sin J Lee
(74) *Attorney, Agent, or Firm* — POLSINELLI PC

(57) ABSTRACT

Cosmetic emulsion containing a gemini surfactant and a lipophilic polymer The invention relates to a composition in the form of an emulsion, in particular in the form of an oil-in-water emulsion, comprising a gemini surfactant having a specific chemical structure with at least two fatty amide groups and at least one lipophilic polymer comprising at least hydroxyethyl acrylate units and acrylate units bearing a lipophilic group, wherein the weight ratio of the sum of all the hydroxyethyl acrylate units to the sum of all the acrylate units bearing a lipophilic group ranges from 1:30 to 1:1 and wherein the lipophilic polymer has a number-average molecular weight Mn ranging from 2000 to 9000 g/mol. The composition in accordance with the invention makes it possible to obtain a cosmetic emulsion having an increased sun protection factor, while at the same time having good cosmetic properties, such as a non-greasy and non-tacky feel, while at the same time being stable, in particular from the physicochemical viewpoint.

14 Claims, No Drawings

(56) References Cited

FOREIGN PATENT DOCUMENTS

| | | |
|---|---|---|
| JP | 2015131767 A | 7/2015 |
| JP | 2015-164970 A | 9/2015 |
| WO | WO 2007/133720 A2 | 11/2007 |
| WO | WO 2011/104228 A1 | 9/2011 |
| WO | WO 2016 098456 A1 | 6/2016 |

OTHER PUBLICATIONS

Derwent English abstract for JP 2012-144580 (Sekiguchi et al) (Year: 2012).*
Machine-assisted English translation for JP 2015-131767 (Sase et al) (Year: 2015).*
Machine-assisted English translation for JP 2012-144580 (Sekiguchi et al) (Year: 2012).*

* cited by examiner

COSMETIC EMULSION CONTAINING A GEMINI SURFACTANT AND A LIPOPHILIC POLYMER

CROSS REFERENCE TO RELATED APPLICATIONS

This application is a National Phase filing under 35 U.S.C. § 371 of PCT/EP2018/081467 filed on 15 Nov. 2018, which application in turn claims priority to Application No. 1760735 filed in France on 15 Nov. 2017. The entire contents of each application are hereby incorporated by reference.

The present application relates to a composition in the form of an emulsion comprising at least one UV-screening agent, at least one gemini surfactant which has a specific chemical structure with at least two fatty amide groups, and at least one lipophilic polymer which has been suitably selected, and to the use of said composition in the cosmetics and dermatology fields, in particular for caring for, treating keratin materials, and in particular for caring for, protecting and/or making up bodily or facial skin, or for hair care.

The vast majority of photoprotective compositions are in the form of an emulsion of O/W type, and contain, at various concentrations, one or more liposoluble conventional organic screening agents and/or one or more water-soluble conventional organic screening agents and/or one or more mineral screening agents.

These compositions are capable of selectively absorbing harmful UV radiation, these screening agents and the amount thereof being selected as a function of the sun protection factor (SPF) desired.

However, the cosmetic properties of photoprotective agents are often judged to be insufficient; they are sometimes found to be too greasy and too tacky, and the SPF boosters known from the prior art do not always improve these properties, or even degrade them.

There is therefore a need to obtain photoprotective compositions which have photoprotective indices that are improved or in any event greater than those that can be obtained with photoprotective systems alone, while at the same time having advantageous cosmetic properties or an undegraded cosmetic attractiveness, and satisfactory physicochemical stability for the use of a product on the market.

Surprisingly, the applicant has discovered that the combination of at least one gemini surfactant which has a specific chemical structure with at least two fatty amide groups and of a lipophilic polymer which has been suitably selected, in a cosmetic composition in the form of an emulsion comprising a photoprotective system capable of screening out UV radiation, makes it possible to solve the problem set out above.

Thus, a subject of the present invention is a composition in the form of an emulsion comprising at least one UV-screening agent, at least one gemini surfactant having the chemical formula below, and also the stereoisomers thereof:

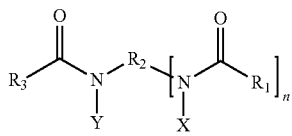

(I)

in which:
a) $R_1$ denotes an alkyl radical having from 1 to 25 carbon atoms or a radical having the formula below:

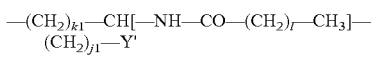

b) $R_3$ denotes an alkyl radical having from 1 to 25 carbon atoms or a radical having the formula below:

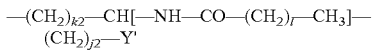

c) $R_2$ denotes a spacer constituted of a linear or branched alkylene chain having from 1 to 12 carbon atoms or of a radical of formula $-CH(Y')-(CH_2)_{n'}-$;
with:
n' representing an integer between 1 and 8, preferably between 3 and 5, and even more preferentially equal to 4;
Y' representing, independently of one another, a carboxylic acid group or an alkaline salt of a carboxylic acid group, such as a sodium salt of a carboxylic acid group;
j1, k1, j2 and k2 representing an integer such that (j1, k1, j2, k2)=(2, 0, 2, 0), (2, 0, 0, 2), (0, 2, 2, 0) or (0, 2, 0, 2); and
l representing an integer from 6 to 16, preferably from 8 to 14, and more preferably from 10 to 12; and
d) X and Y denote, independently of each other, a $(C_2H_4O)_a-(C_3H_6O)_bZ$, in which
Z denotes a hydrogen atom or a radical $-CH_2-COOM$, $-SO_3M$, $-P(O)(OM)_2$, $-C_2H_4-SO_3M$, $-C_3H_6-SO_3M$ or $-CH_2(CHOH)_4CH_2OH$, where M represents H or an alkali metal or alkaline-earth metal or ammonium or alkanolammonium ion,
a ranges from 0 to 15,
b ranges from 0 to 10, and
the sum of a+b ranges from 1 to 25; and
e) n ranges from 1 to 10; and
at least one lipophilic polymer comprising monomeric units of formulae (A) and (B):

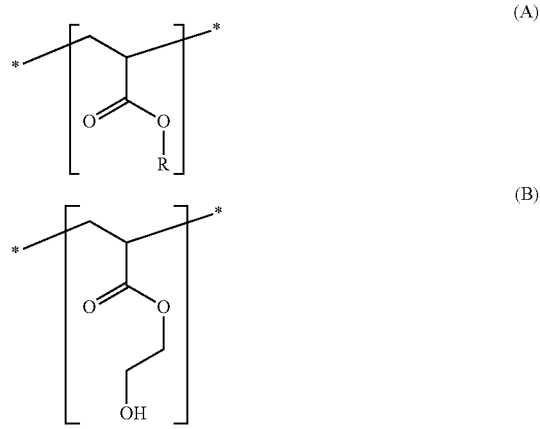

in which:
R, independently of one another, are chosen from alkyl or alkylene radicals; with at least 60% by weight of the R groups being behenyl radicals, the percentage by weight relating to the sum of all the R groups present in the polymer;
the weight ratio of the sum of all the hydroxyethyl acrylate units to the sum of all the acrylate units bearing the R group ranges from 1:30 to 1:1; and the sum of the total units A and B is at least 95% by weight of the total weight of the polymer.

The composition in accordance with the invention makes it possible to obtain a cosmetic emulsion having an increased sun protection factor, while at the same time having good cosmetic properties, such as a non-greasy and non-tacky feel, and at the same time being stable, in particular from the physicochemical viewpoint.

The emulsion obtained according to the invention has good stability over time, even at a temperature above ambient temperature (for example 45° C.).

The term "stable emulsion" is intended to mean an emulsion which exhibits no macroscopic and microscopic change (in colour, in odour, in viscosity, nor any variation in pH) after storage and/or temperature change, in particular after 24 hours at a temperature equal to ambient temperature (AT), at 4° C. or at 45° C.

A subject of the invention is also a cosmetic treatment process for caring for and/or making up keratin materials, which consists in applying to the keratin materials a composition as defined above.

A subject of the invention is also the use of said composition in the cosmetics or dermatology field, and in particular for caring for, protecting and/or making up keratin materials, such as bodily or facial skin, or the hair.

The composition according to the invention is intended for topical application and thus comprises a physiologically acceptable medium. The term "physiologically acceptable medium" here is understood to mean a medium that is compatible with keratin materials.

In the context of the present invention, the term "keratin material" especially is understood to mean the skin, the scalp, keratin fibres such as the eyelashes, the eyebrows, head hair, bodily hair, the nails, and mucous membranes such as the lips, and more particularly the skin (body, face, area around the eyes, eyelids).

In the following text, the expression "at least one" is equivalent to "one or more" and, unless otherwise indicated, the limits of a range of values are included in that range.

Gemini Surfactants Comprising at Least Two Fatty Amide Groups

The composition in accordance with the invention comprises at least one gemini surfactant having the chemical formula below, and also the stereoisomers thereof:

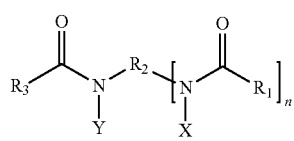

(I)

in which:
a) $R_1$ denotes an alkyl radical having from 1 to 25 carbon atoms or a radical having the formula below:

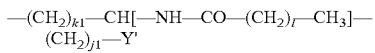
—$(CH_2)_{k1}$—CH[—NH—CO—$(CH_2)_l$—$CH_3$]—$(CH_2)_{j1}$—Y' b) $R_3$ denotes an alkyl radical having from 1 to 25 carbon atoms or a radical having the formula below:

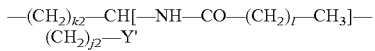
—$(CH_2)_{k2}$—CH[—NH—CO—$(CH_2)_l$—$CH_3$]—$(CH_2)_{j2}$—Y' c) $R_2$ denotes a spacer constituted of a linear or branched alkylene chain having from 1 to 12 carbon atoms or of a radical of formula —CH(Y')—$(CH_2)_{n'}$—;

with:
n' representing an integer between 1 and 8, preferably between 3 and 5, and even more preferentially equal to 4;
Y' representing, independently of one another, a carboxylic acid group or an alkaline salt of a carboxylic acid group, such as a sodium salt of a carboxylic acid group;
j1, k1, j2 and k2 representing an integer such that (j1, k1, j2, k2)=(2, 0, 2, 0), (2, 0, 0, 2), (0, 2, 2, 0) or (0, 2, 0, 2); and
l representing an integer from 6 to 16, preferably from 8 to 14, and more preferably from 10 to 12; and
d) X and Y denote, independently of each other, a $(C_2H_4O)_a$—$(C_3H_6O)_b$Z, in which
Z denotes a hydrogen atom or a radical —$CH_2$—COOM, —$SO_3M$, —P(O)(OM)$_2$, —$C_2H_4$—$SO_3M$, —$C_3H_6$—$SO_3M$ or —$CH_2$(CHOH)$_4$CH$_2$OH, where M represents H or an alkali metal or alkaline-earth metal or ammonium or alkanolammonium ion,
a ranges from 0 to 15,
b ranges from 0 to 10, and
the sum of a+b ranges from 1 to 25; and
e) n ranges from 1 to 10.

According to a first embodiment of the invention, the gemini surfactant(s) are chosen from the compounds of formula (II), and also the stereoisomers thereof:

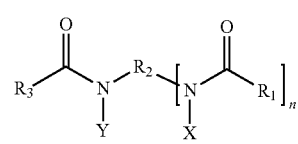

(II)

in which:
$R_1$ and $R_3$ denote, independently of each other, an alkyl radical containing from 1 to 25 carbon atoms;
$R_2$ denotes a spacer constituted of a linear or branched alkylene chain containing from 1 to 12 carbon atoms;
d) X and Y denote, independently of each other, a —$(C_2H_4O)_a$—$(C_3H_6O)_b$Z, in which
Z denotes a hydrogen atom or a radical —$CH_2$—COOM, —$SO_3M$, —P(O)(OM)$_2$, —$C_2H_4$—$SO_3M$, —$C_3H_6$—$SO_3M$ or —$CH_2$(CHOH)$_4$CH$_2$OH, where M represents H or an alkali metal or alkaline-earth metal or ammonium or alkanolammonium ion,
a ranges from 0 to 15,
b ranges from 0 to 10, and
the sum of a+b ranges from 1 to 25; and
n ranges from 1 to 10.

According to one preferred embodiment, the gemini surfactant(s) of formula (II) are such that each of the groups $R_1$—CO— and $R_3$—CO— comprises from 8 to 20 carbon atoms, and preferably denotes a coconut fatty acid residue (mainly comprising lauric acid and myristic acid).

According to another preferred embodiment, the gemini surfactant(s) of formula (II) are such that, for each of the X and Y radicals, the sum of a and b has an average value ranging from 10 to 20 and is preferably equal to 15. A preferred group for Z is the group —$SO_3M$, where M is preferably an alkali metal ion, such as a sodium ion.

In formula (II) as defined above, the spacer $R_2$ is advantageously constituted of a linear $C_1$-$C_3$ alkylene chain, and preferably a ($CH_2CH_2$) ethylene chain.

Finally, n is advantageously equal to 1.

A surfactant of this type is in particular the one identified by the INCI name: Sodium dicocoylethylenediamine PEG-15 sulfate, having the following structure:

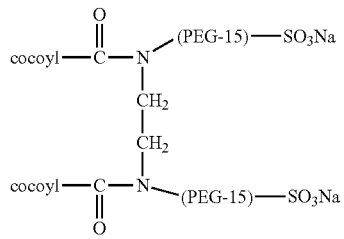

it being understood that PEG represents the group $CH_2CH_2O$ and cocoyl represents the coconut fatty acid residue.

This surfactant has a molecular structure very similar to that of ceramide-3.

Preferably, the gemini surfactant of formula (II) of the invention is used as a mixture with other surfactants, and in particular as a mixture with (a) a glyceryl ester of a $C_6$-$C_{22}$ fatty acid (preferably $C_{14}$-$C_{20}$ such as a stearate), (b) a diester of a $C_6$-$C_{22}$ fatty acid (preferably $C_{14}$-$C_{20}$ such as a stearate) and of citric acid and of glycerol, and (c) a $C_{10}$-$C_{30}$ fatty alcohol (preferably behenyl alcohol).

More preferentially, the gemini surfactant of formula (II) according to the invention represents from 10% to 20% by weight and advantageously 15% by weight; the glyceryl ester of a $C_6$-$C_{22}$ fatty acid represents from 30% to 40% by weight, advantageously 35% by weight; the diester of a $C_6$-$C_{22}$ fatty acid and of citric acid and of glycerol represents from 10% to 20% by weight, advantageously 15% by weight; and the $C_{10}$-$C_{30}$ fatty alcohol represents from 30% to 40% by weight, advantageously 35% by weight, relative to the total weight of the mixture of surfactants containing the gemini surfactant.

As a variant, the gemini surfactant of formula (II) according to the invention may be used as a mixture with an anionic surfactant, such as an ester of lauric acid, sodium auryl lactate. In this case, the gemini surfactant preferably represents from 30 to 50% by weight, and the anionic surfactant represents from 30 to 50% by weight, relative to the total weight of the mixture.

The gemini surfactant may be used, for example, as a mixture with other surfactants in the form of the products sold by the company Sasol under the Ceralution® names, and in particular the following products:
Ceralution® H: Behenyl Alcohol, Glyceryl Stearate, Glyceryl Stearate Citrate and Sodium Dicocoylethylenediamine PEG-15 Sulfate,
Ceralution® F: Sodium Lauroyl Lactylate and Sodium Dicocoylethylenediamine PEG-15 Sulfate,
Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names).

According to one particular embodiment of the invention, the gemini surfactant(s) of formula (II) are in the form of a mixture of surfactants comprising from 3% to 50% by weight of gemini surfactants of formula (II), preferably from 10% to 50% by weight, and even more preferentially from 10% to 20% by weight, relative to the total weight of the mixture.

The gemini surfactant(s) of formula (II) can be present in the composition according to the invention in a content of active material ranging from 0.01% to 5% by weight, relative to the total weight of the composition, preferably ranging from 0.1% to 3% by weight and better still ranging from 0.2% to 1.5% by weight.

According to second embodiment of the invention, the gemini surfactant(s) are chosen from the compounds of formula (III), and also the stereoisomers thereof:

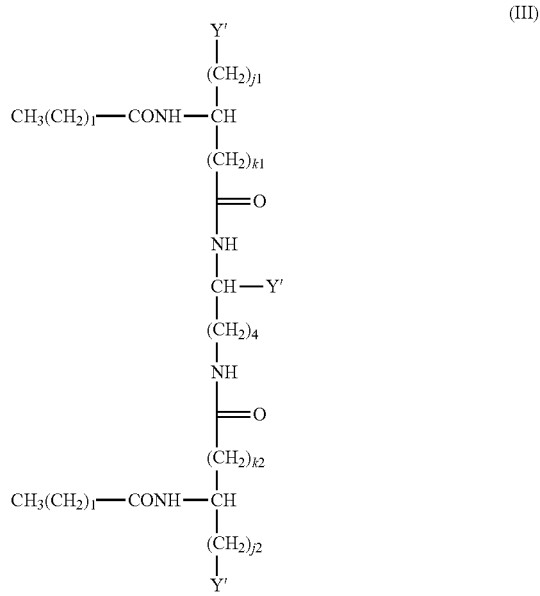

in which:
Y' represent, independently of one another, a carboxylic acid group or an alkaline salt of a carboxylic acid group, such as a sodium salt of a carboxylic acid group;
j1, k1, j2 and k2 represent an integer such that (j1, k1, j2, k2)=(2, 0, 2, 0), (2, 0, 0, 2), (0, 2, 2, 0) or (0, 2, 0, 2); and
l represents an integer from 6 to 16, preferably from 8 to 14, and more preferably from 10 to 12.

According to one particular embodiment of the invention, in formula (III), l represents an integer ranging from 8 to 12, j1=j2=0, and k1=k2=2.

Preferably, in formula (III), Y' represents —COONa, j1=j2=0, k1=k2=2; and l=10.

By way of examples of gemini surfactants of formula (III), mention may be made of sodium dilauramidoglutamide lysine, sodium dimyristoylglutamide lysine and sodium distearoylglutamide lysine. Sodium dilauramidoglutamide lysine is particularly preferred. Sodium dilauramidoglutamide lysine is in particular sold by the company Asahi Kasei Chemicals under the names Pellicer L-30 and Pellicer LB-10.

The gemini surfactant(s) of formula (III) is (are) in particular described in application WO 2004/020394.

The gemini surfactant(s) comprising at least two fatty amide groups of formula (III) can be present in the composition in an amount of active material ranging from 0.01% to 5% by weight, preferably from 0.01% to 1% by weight, and even more preferentially from 0.01% to 0.7% by weight, relative to the total weight of the composition.

According to one preferred embodiment, the gemini surfactant(s) present in the composition in accordance with the invention are chosen from the compounds of formula (II) as defined above, and also the stereoisomers thereof.

Lipophilic Polymers

The composition in accordance with the invention comprises at least one lipophilic polymer comprising monomeric units of formulae (A) and (B):

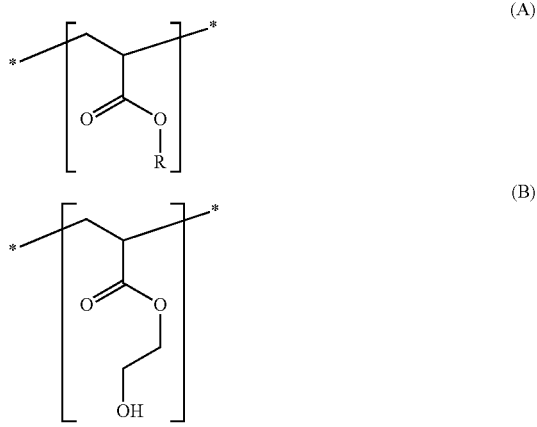

in which:

R, independently of one another, are chosen from alkyl or alkylene radicals;

with at least 60% by weight of the R groups being behenyl radicals, the percentage by weight relating to the sum of all the R groups present in the polymer;

the weight ratio of the sum of all the hydroxyethyl acrylate units to the sum of all the acrylate units bearing the R group ranges from 1:30 to 1:1; and the sum of the total units A and B is at least 95% by weight of the total weight of the polymer.

Preferably, R is constituted of alkyl radicals, preferably of $C_{16}$-$C_{22}$ alkyl radicals, and more preferentially of behenyl ($C_{22}$) radicals.

Preferably, at least 70% by weight of the R groups are behenyl radicals, preferentially at least 80% by weight, and more preferentially at least 90% by weight.

According to one preferred embodiment, all the R groups are behenyl radicals.

Preferably, said weight ratio ranges from 1:15 to 1:1, preferentially ranges from 1:10 to 1:4.

Advantageously, the polymeric units present in the polymer are constituted of the units (A) and (B) previously described.

The polymer has a number-average molecular weight Mn ranging from 2000 to 9000 g/mol, preferably ranging from 5000 to 9000 g/mol. The number-average molecular weight can be measured with the gel permeation chromatography method, for example according to the method described in the example hereinafter.

Preferably, the polymer has a melting point ranging from 60° C. to 69° C., and preferentially ranging from 63° C. to 67° C. The melting point is measured by differential scanning calorimetry (DSC), for example according to the method described in the example hereinafter.

The polymer used according to the invention can be prepared by polymerization of the monomer of formula $CH_2=CH-COO-R$, R having the meaning previously described, and of 2-hydroxyethyl acrylate.

The polymerization can be carried out according to known methods, such as solution polymerization or emulsion polymerization.

The polymerization is, for example, described in document US 2007/0264204.

The lipophilic polymer(s) used in the context of the invention and as previously described can be present in the composition in an amount of active material ranging from 0.1% to 10% by weight, preferably from 0.1% to 3% by weight, relative to the total weight of the composition.

UV-Screening Agents

The composition in accordance with the invention comprises one or more UV-screening agents. Said UV-screening agents can be chosen from water-soluble, liposoluble or insoluble organic UV-screening agents and/or mineral pigments. Preferentially, the composition according to the invention comprises at least one hydrophilic, lipophilic or insoluble organic UV-screening agent.

The term "water-soluble UV-screening agent" is intended to mean any cosmetic or dermatological organic or inorganic compound for screening out UV radiation, which can be fully dissolved in molecular form or miscibilized in a liquid aqueous phase or else can be dissolved in colloidal form (for example in micellar form) in a liquid aqueous phase.

The term "liposoluble screening agent" is intended to mean any cosmetic or dermatological, organic or inorganic compound for screening out UV radiation which can be fully dissolved in molecular form or misciblized in an oily phase or else can be dissolved in colloidal form (for example in micellar form) in an oily phase.

The term "insoluble UV-screening agent" is intended to mean any cosmetic or dermatological organic or mineral compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to ambient temperature.

a) Organic UV-Screening Agents

The organic UV-screening agents are in particular chosen from cinnamic compounds; dibenzoylmethane compounds; anthranilate compounds; salicylic compounds; benzylidenecamphor compounds; benzophenone compounds; β,β-diphenyl acrylate compounds; triazine compounds; benzotriazole compounds, in particular the silicone benzotriazoles described in patent EP0392883 and the methylenebis(hydroxyphenyl benzotriazole) compounds as described in applications U.S. Pat. Nos. 5,237,071, 5,166,355, GB2303549, DE 197 26 184 and EP893119; benzalmalonate compounds, in particular those mentioned in U.S. Pat. No. 5,624,663; benzimidazole derivatives; imidazoline compounds; the bis-benzoazolyl compounds as described in patents EP669323 and U.S. Pat. No. 2,463,264; p-aminobenzoic (PABA) compounds; the benzoxazole compounds as described in patent applications EP0832642, EP1027883, EP1300137 and DE10162844; screening polymers and screening silicones such as those described in particular in application WO-93/04665; α-alkylstyrene-based dimers, such as those described in patent application DE19855649; 4,4-diarylbutadiene compounds such as those described in applications EP0967200, DE19746654, DE19755649, EP-A-1008586, EP1133980 and EP133981; merocyanine compounds as described in U.S. Pat. No. 4,195,999, application WO2004/006878, applications WO2008/090066, WO2011113718, WO2009027258, WO2013010590, WO2013011094, WO2013011480 and the documents IP COM Journal N° 000179675D published on 23 Feb. 2009, IP COM Journal N° 000182396D published on 29 Apr. 2009, IP COM Journal N° 000189542D published on 12 Nov. 2009, and IP COM Journal N° IPCOM000011179D published on Apr. 3, 2004, and mixtures thereof.

As examples of organic photoprotective agents, mention may be made of those denoted hereinbelow under their INCI name:

Dibenzoylmethane Compounds
 Butyl methoxydibenzoylmethane sold in particular under the trade name Parsol 1789® by DSM Nutritional Products, Inc.

Cinnamic Compounds:
 Ethylhexyl methoxycinnamate, sold in particular under the trade name Parsol MCX® by DSM Nutritional Products,
 Isopropyl methoxycinnamate,
 Isoamyl p-methoxycinnamate sold under the trade name Neo Heliopan E 1000® by Symrise,
 DEA methoxycinnamate,
 Diisopropyl methylcinnamate,
 Glyceryl ethylhexanoate dimethoxycinnamate.

Para-Aminobenzoic Compounds:
 PABA,
 Ethyl PABA,
 Ethyl dihydroxypropyl PABA,
 Ethylhexyl dimethyl PABA, sold in particular under the name Escalol 507® by ISP,
 Glyceryl PABA,
 PEG-25 PABA, sold under the name Uvinul P 25® by BASF.

Salicylic Compounds:
 Homosalate, sold under the name Eusolex HMS® by Rona/EM Industries,
 Ethylhexyl salicylate, sold under the name Neo Heliopan OS® by Symrise,
 Dipropylene glycol salicylate, sold under the name Dipsal® by Scher,
 TEA salicylate, sold under the name Neo Heliopan TS® by Symrise, β,β-Diphenyl Acrylate Compounds:
 Octocrylene, sold in particular under the trade name Uvinul N 539® by BASF,
 Etocrylene, sold in particular under the trade name Uvinul N 35® by BASF.

Benzophenone Compounds:
 Benzophenone-1 sold under the trade name Uvinul 400® by BASF,
 Benzophenone-2, sold under the trade name Uvinul D 50® by BASF,
 Benzophenone-3 or Oxybenzone, sold under the trade name Uvinul M 40® by BASF,
 Benzophenone-4, sold under the trade name Uvinul MS 40® by BASF,
 Benzophenone-5,
 Benzophenone-6 sold under the trade name Helisorb 11® by Norquay,
 Benzophenone-8, sold under the trade name Spectra-Sorb UV-24® by American Cyanamid,
 Benzophenone-9, sold under the trade name Uvinul DS 49® by BASF,
 Benzophenone-12,
 n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
 1,1'-(1,4-Piperazinediyl)bis[1-[2-[4-(diethylamino)-2-hydroxybenzoyl]phenyl]methanone](CAS 919803-06-8), such as described in patent application WO 2007/071 584; this compound advantageously being used in micronized form (average size of 0.02 to 2 µm), which may be obtained, for example, according to the micronization process described in patent applications GB-A-2 303 549 and EP-A-893 119, and in particular in the form of an aqueous dispersion.

Benzylidenecamphor Compounds:
 3-Benzylidenecamphor, manufactured under the name Mexoryl SD® by Chimex,
 4-Methylbenzylidenecamphor, sold under the name Eusolex 6300® by Merck,
 Benzylidenecamphorsulfonic acid, manufactured under the name Mexoryl SL® by Chimex,
 Camphor benzalkonium methosulfate, manufactured under the name Mexoryl SO® by Chimex,
 Terephthalylidenedicamphorsulfonic acid, manufactured under the name Mexoryl SX® by Chimex,
 Polyacrylamidomethylbenzylidenecamphor, manufactured under the name Mexoryl SW® by Chimex.

Phenylbenzimidazole Compounds:
 Phenylbenzimidazolesulfonic acid, sold in particular under the trade name Eusolex 232® by Merck.

Bis-Benzoazolyl Compounds
 Disodium phenyl dibenzimidazole tetrasulfonate, sold under the trade name Neo Heliopan AP® by Symrise.

Benzotriazole Compounds
 Drometrizole trisiloxane, manufactured under the name Mexoryl SX® by Chimex; Methylenebis(benzotriazolyl) tetramethylbutylphenol, in particular in solid form, such as the product sold under the trade name Mixxim BB/100® by Fairmount Chemical, or in the form of an aqueous dispersion of micronized particles with an average particle size ranging from 0.01 to 5 µm, more preferentially from 0.01 to 2 µm and more particularly from 0.020 to 2 µm, with at least one alkylpolyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by the company BASF, or in the form of an aqueous dispersion of micronized particles with an average particle size ranging from 0.02 to 2 µm, more preferentially from 0.01 to 1.5 µm and more particularly from 0.02 to 1 µm, in the presence of at least one polyglyceryl mono($C_8$-$C_{20}$) alkyl ester with a degree of glycerol polymerization of at least 5, such as the aqueous dispersions described in patent application WO 2009/063 392.

Triazine Compounds:
 Bis-ethylhexyloxyphenol methoxyphenyl triazine, sold under the trade name Tinosorb S® by BASF,
 Ethylhexyl triazone, sold in particular under the trade name Uvinul T150® by BASF,
 Diethylhexyl butamido triazone, sold under the trade name Uvasorb HEB® by Sigma 3V,
 2,4,6-Tris(dineopentyl 4'-aminobenzalmalonate)-s-triazine,
 2,4,6-Tris(diisobutyl 4'-aminobenzalmalonate)-s-triazine,
 2,4-bis(n-butyl 4'-aminobenzoate)-6-(aminopropyltrisiloxane)-s-triazine,
 2,4-bis(dineopentyl 4'-aminobenzalmalonate)-6-(n-butyl 4'-aminobenzoate)-s-triazine, symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC West Henrietta, NY, US (20 Sep. 2004), especially 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 µm), which may be obtained, for example, according to the micronization process described in patent applications GB-A-2 303 549 and EP-A-893 119, and especially in aqueous dispersion;

silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy]disiloxanyl}propyl)amino]-s-triazine.

Anthranilic Compounds:
Menthyl anthranilate, sold under the trade name Neo Heliopan MA® by Symrise.

Imidazoline Compounds:
Ethylhexyl dimethoxybenzylidene dioxoimidazoline propionate, Benzalmalonate Compounds:
Polyorganosiloxane containing benzalmalonate functions, for instance Polysilicone-15,
sold under the trade name Parsol SLX® by DSM Nutritional Products, Inc.

4,4-Diarylbutadiene Compounds:
1,1-Dicarboxy(2,2'-dimethylpropyl)-4,4-diphenylbutadiene.

Benzoxazole Compounds:
2,4-Bis[5-(1,1-dimethylpropyl)benzoxazol-2-yl(4-phenyl)imino]-6-(2-ethylhexyl)imino-1,3,5-triazine, sold under the name Uvasorb K2A® by Sigma 3V.

The preferential organic screening agents are chosen from:
Butyl methoxydibenzoylmethane
Ethylhexyl methoxycinnamate
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Bis-ethylhexyloxyphenol methoxyphenyl triazine,
Ethylhexyl triazone
Diethylhexyl butamidotriazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(diphenyl)triazine,
2,4,6-Tris(terphenyl)triazine,
Drometrizoletrisiloxane,
Polysilicone-15,
1,1-Dicarboxy(2,2'-dimethylpropyl)-4,4-diphenylbutadiene,
2,4-bis[5-(1-Dimethylpropyl)benzoxazol-2-yl-(4-phenyl)imino]-6-(2-ethylhexyl)imino-1,3,5-triazine,
and mixtures thereof.

The particularly preferred organic screening agents are chosen from:
Butyl methoxydibenzoylmethane
Ethylhexyl salicylate,
Homosalate,
Octocrylene,
n-Hexyl 2-(4-diethylamino-2-hydroxybenzoyl)benzoate,
Terephthalylidenedicamphorsulfonic acid,
Bis-ethylhexyloxyphenol methoxyphenyl triazine,
Ethylhexyl triazone
Diethylhexyl butamidotriazone,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
Drometrizole trisiloxane,
and mixtures thereof.

b) Inorganic UV-Screening Agents

The mineral UV-screening agents used in accordance with the present invention are metal oxide pigments. More preferentially, the inorganic UV-screening agents of the invention are metal oxide particles with a mean elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
with silica, such as the product Sunveil® from the company Ikeda,
with silica and iron oxide, such as the product Sunveil F® from the company Ikeda,
with silica and alumina, such as the products Microtitanium Dioxide MT 500 SA® and Microtitanium Dioxide MT 100 SA from the company Tayca and Tioveil from the company Tioxide, with alumina, such as the products Tipaque TTO-55 (B)® and Tipaque TTO-55 (A)® from the company Ishihara and UVT 14/4 from the company Sachtleben Pigments, with alumina and aluminium stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck, with silica, alumina and alginic acid, such as the product MT-100 AQ® from the company Tayca, with alumina and aluminium laurate, such as the product Microtitanium Dioxide MT 100 S® from the company Tayca, with iron oxide and iron stearate, such as the product Microtitanium Dioxide MT 100 F® from the company Tayca, with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca, $TiO_2$ treated with octyltrimethylsilane, sold under the trade name T 805® by the company Degussa Silices, $TiO_2$ treated with a polydimethylsiloxane, sold under the trade name 70250 Cardre UF TiO2SI3® by the company Cardre, anatase/rutile $TiO_2$ treated with a polydimethylhydrogenosiloxane, sold under the trade name Microtitanium Dioxide USP Grade Hydrophobic® by the company Color Techniques.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wacker under the name Transparent titanium oxide PW®, by the company Miyoshi Kasei under the name UFTR®, by the company Tomen under the name ITS® and by the company Tioxide under the name Tioveil AQ.

The uncoated zinc oxide pigments are, for example:

those sold under the name Z-Cote by the company Sunsmart;

those sold under the name Nanox® by the company Elementis;

those sold under the name Nanogard WCD 2025® by the company Nanophase Technologies.

The coated zinc oxide pigments are, for example:

those sold under the name Zinc Oxide CS-5® by the company Toshibi (ZnO coated with polymethylhydrogenosiloxane);

those sold under the name Nanogard Zinc Oxide FN® by the company Nanophase Technologies (as a 40% dispersion in Finsolv TN, $C_{12}$-$C_{15}$ alkyl benzoate);

those sold under the name Daitopersion Zn-30® and Daitopersion Zn-50® by Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO® by the company Daikin (ZnO coated with perfluoroalkyl phosphate and copolymer based on perfluoroalkylethyl as a dispersion in cyclopentasiloxane);

those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in the ethylhexyl methoxycinnamate/PVP-hexadecene copolymer/methicone mixture);

those sold under the name Fuji ZnO-SMS-10® by the company Fuji Pigment (ZnO coated with silica and polymethylsilsesquioxane);

those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556), Nanogard FE 45 BL 345® and Nanogard FE 45 BL® or by the company BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The UV-screening agents according to the invention are generally present in the composition according to the invention in a content ranging from 0.1% to 45% by weight and in particular from 1% to 30% by weight relative to the total weight of the composition.

The composition according to the invention is in the form of an emulsion and can be prepared according to the usual methods.

According to one particular embodiment, the composition according to the invention is in the form of an oil-in-water emulsion (direct emulsion) comprising a continuous aqueous phase and an oily phase dispersed in said aqueous phase.

According to another particular embodiment, the composition according to the invention is in the form of a water-in-oil emulsion (inverse emulsion) comprising a continuous oily phase and an aqueous phase dispersed in said oily phase.

Preferably, the composition according to the invention is in the form of an oil-in-water emulsion.

This emulsion can have a texture ranging from fluid to thick. It can for example have a viscosity at ambient temperature (25° C.) which ranges within a very broad range, for example a viscosity ranging from approximately 1 to 500 poises (0.1 to 50 Pa·s), and preferably from approximately 2 to 10 poises (0.2 to 1 Pa·s). The viscosity measurement is generally carried out at 25° C., using a Rheomat RM180® viscometer equipped with a No. 1, 2, 3 or 4 spindle depending on the viscosity range, the measurement being carried out after 10 minutes of rotation of the spindle in the composition (after which time stabilization of the viscosity and of the speed of rotation of the spindle are observed), at a shear rate of $2005\ s^{-1}$.

Fatty Phase

The composition according to the invention comprises at least one fatty phase.

The proportion of the fatty phase can range for example from 1% to 80% by weight, preferably from 5% to 40% by weight, relative to the total weight of the composition.

For the purposes of the invention, the fatty phase includes any fatty substance that is liquid at ambient temperature and atmospheric pressure, generally oils, or that is solid at ambient temperature and atmospheric pressure, like pasty compounds or waxes.

For the purposes of the present invention, the term "pasty compound" is intended to mean a compound that is water-immiscible and that undergoes a reversible solid/liquid change of state and that comprises in the solid state an anisotropic crystal organization, and comprises, at a temperature of 23° C., a liquid fraction and a solid fraction.

For the purposes of the present invention, the term "wax" is understood to mean a lipophilic compound, which is solid at ambient temperature (25° C.), with a reversible solid/liquid change of state, which has a melting point of greater than or equal to 30° C. that may be up to 120° C.

The melting point of the wax may be measured using a differential scanning calorimeter (D.S.C.), for example the calorimeter sold under the name DSC 30 by the company Mettler.

Preferably, the measuring protocol is as follows:

A sample of 5 mg of wax placed in a crucible is subjected to a first temperature rise passing from −20° C. to 100° C., at a heating rate of 10° C./minute, it is then cooled from 100° C. to −20° C. at a cooling rate of 10° C./minute and is finally subjected to a second temperature rise passing from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

By way of pasty compounds, mention may be made of synthetic fatty substances and fatty substances of plant origin. The latter can be obtained by synthesis from starting materials of plant origin.

The solid fatty substance is advantageously chosen from:
lanolin and derivatives thereof,
polyol ethers chosen from pentaerythrityl ethers of a polyalkylene glycol, fatty alkyl ethers of a sugar, and mixtures thereof, the pentaerythrityl ether of polyethylene glycol comprising 5 oxyethylene units (5 OE) (CTFA name: PEG-5 Pentaerythrityl Ether), polypropylene glycol pentaerythrityl ether comprising 5 oxypropylene units (5 OP)(CTFA name: PEG-5 Pentaerythrityl Ether), and mixtures thereof, and more especially the PEG-5 Pentaerythrityl Ether, PPG-5 Pentaerythrityl Ether and soybean oil mixture sold under the Lanolide name by Vevy, which is a mixture in which the constituents are in a 46/46/8 ratio by weight: 46% PPG-5 pentaerythrityl ether, 46% PPG-5 pentaerythrityl ether and 8% soybean oil,
polymeric or non-polymeric silicone compounds,
polymeric or non-polymeric fluorinated compounds,
vinyl polymers, especially:
olefin homopolymers and copolymers,
hydrogenated diene homopolymers and copolymers,
linear or branched homo- or copolymer oligomers of alkyl (meth)acrylates preferably having a $C_3$-$C_{30}$ alkyl group,
homopolymer and copolymer oligomers of vinyl esters bearing $C_3$-$C_{30}$ alkyl groups,
homo- and copolymer oligomers of vinyl ethers having $C_3$-$C_{30}$ alkyl groups,
liposoluble polyethers resulting from polyetherification between one or more $C_2$-$C_{100}$ and preferably $C_2$-$C_{50}$ diols.
esters,
and/or mixtures thereof.

The solid fatty substance may be a polymer, in particular a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide with the alkylene oxides in the copolymer is from 5:95 to 70:30. In this family, mention will be made especially of copolymers such as long-chain alkylene oxides arranged in blocks with an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by AkzoNobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythrityl esters,
esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl isostearyl dimer dilinoleate (Lusplan PI-DA, Lusplan PHY/IS-DA), phytosteryl/isostearyl/cetyl/stearyl/behenyl dimer dilinoleate (Plandool H or Plandool S), and mixtures thereof,
hydrogenated soybean oil, hydrogenated coconut oil, hydrogenated rape seed oil, mixtures of hydrogenated vegetable oils such as the mixture of hydrogenated soybean, coconut, palm and rapeseed vegetable oil, for example the mixture sold under the reference Akogel® by the company AarhusKarlshamn (INCI name: Hydrogenated Vegetable Oil),
shea butter, in particular the product of which the INCI name is *Butyrospermum parkii* Butter, such as the product sold under the reference Sheasoft® by the company AarhusKarlshamn,
cocoa butter, in particular the product which is sold under the name CT Cocoa Butter Deodorized by the company Dutch Cocoa BV or the product which is sold under the name Beurre De Cacao NCB HD703 758 by the company Barry Callebaut,
shorea butter, in particular the product which is sold under the name Dub Shorea T by the company Stearineries Dubois,
and mixtures thereof.

According to one embodiment, the composition may comprise from 0.5 to 30% by weight of pasty compounds relative to the total weight of the composition.

The waxes that may be used in a composition according to the invention are chosen from waxes that are solid at ambient temperature, of animal, plant, mineral or synthetic origin, and mixtures thereof. They may be hydrocarbon-based, fluoro and/or silicone waxes.

Examples that may especially be mentioned include hydrocarbon-based waxes, such as natural beeswax (or bleached beeswax), synthetic beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 and 3080 sold by the company Nippon Seiro, ceresins or ozokerites, for instance isoparaffins of which the melting point is below 40° C., such as the product EMW-0003 sold by the company Nippon Seiro, α-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes.

The other solid fatty substances that may be present in the fatty phase are, for example, fatty acids comprising from 8 to 30 carbon atoms, for instance stearic acid, lauric acid or palmitic acid; fatty alcohols comprising from 8 to 30 carbon atoms, for instance stearyl alcohol or cetyl alcohol and mixtures thereof (cetearyl alcohol).

According to one embodiment, the composition may comprise 0.5% (rather 0.2%) to 20% by weight of wax relative to the total weight of the composition.

The fatty phase of the composition in accordance with the invention can also comprise at least one oil. The oil(s) present in the composition may be volatile or non-volatile.

The term "oil" is intended to mean any fatty substance that is in liquid form at ambient temperature (25° C.) and at atmospheric pressure.

The volatile or non-volatile oils may be hydrocarbon-based oils, especially of animal or plant origin, synthetic oils, silicone oils or fluoro oils, or mixtures thereof.

For the purposes of the present invention, the term "silicone oil" is intended to mean an oil comprising at least one silicon atom, and especially at least one Si—O group.

The term "hydrocarbon-based oil" is intended to mean an oil mainly containing hydrogen and carbon atoms and possibly oxygen, nitrogen, sulfur and/or phosphorus atoms.

The term "fluoro oil" is intended to mean an oil comprising at least one fluorine atom and especially at least one perfluorinated chain.

Non-Volatile Oils

For the purposes of the present invention, the term "non-volatile oil" is understood to mean an oil with a vapour pressure of less than 0.13 Pa (0.01 mmHg).

The non-volatile oils may be chosen especially from non-volatile hydrocarbon-based oils, which may be fluorinated, and/or silicone oils.

As non-volatile hydrocarbon-based oils that are suitable for use in the invention, mention may be made especially of:
hydrocarbon-based oils of animal origin,
hydrocarbon-based oils of plant origin such as phytostearyl esters, such as phytostearyl oleate, phytostearyl isostearate and lauroyl/octyldodecyl/phytostearyl glutamate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passion flower oil or musk rose oil; shea butter; or alternatively caprylic/capric acid triglycerides, for instance those sold by Stearineries Dubois or those sold under the names Miglyol 810®, 812® and 818® by Dynamit Nobel; the refined vegetable perhydrosqualene sold under the name Fitoderm by Cognis.

hydrocarbon-based oils of mineral or synthetic origin, for instance:
  synthetic ethers having from 10 to 40 carbon atoms;
  linear or branched hydrocarbons of mineral or synthetic origin, such as petroleum jelly, polydecenes, hydrogenated polyisobutene such as Parleam, and squalane, and mixtures thereof, and in particular hydrogenated polyisobutene;
  synthetic esters, such as the oils of formula $R_1COOR_2$, in which $R_1$ represents the residue of a linear or branched fatty acid comprising from 1 to 40 carbon atoms and $R_2$ represents an especially branched hydrocarbon-based chain containing from 1 to 40 carbon atoms, with the proviso that $R_1+R_2$ is $\geq 10$.

The esters may be chosen in particular from esters, in particular fatty acid esters, for instance:
  cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and in particular isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;
  polyol esters and pentaerythrityl esters, for instance dipentaerythrityl tetrahydroxystearate/tetraisostearate;
  esters of diol dimers and of diacid dimers, such as Lusplan DD-DA5® and Lusplan DD-DA7® sold by Nippon Fine Chemical and described in patent application FR 0302809,
  fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;
  higher fatty acids such as oleic acid, linoleic acid or linolenic acid, and mixtures thereof;
  dialkyl carbonates, the two alkyl chains possibly being identical or different, such as the dicaprylyl carbonate sold under the name Cetiol CC® by Cognis;
  non-volatile silicone oils, for instance non-volatile polydimethylsiloxanes (PDMSs), polydimethylsiloxanes comprising alkyl or alkoxy groups that are on the side and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof;
  and mixtures thereof.

Volatile Oils

For the purposes of the present invention, "volatile oil" is intended to mean an oil (or non-aqueous medium) that is capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa (10- to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms.

The term "hydrocarbon-based oil" is understood to mean an oil formed essentially from, or even constituted of, carbon and hydrogen atoms, and possibly oxygen, nitrogen, sulfur and/or phosphorus atoms, and containing no silicon or fluorine atoms; it may contain ester, ether, amine or amide groups.

The volatile hydrocarbon-based oil(s) can in particular be chosen from volatile branched esters, volatile branched alkanes, volatile linear alkanes, and mixtures thereof.

The compositions according to the invention can comprise one or more branched $C_5$-$C_1$ esters, such as isohexyl neopentanoate, isoamyl esters such as isoamyl laurate, or else isononyl isononanoate.

The composition according to the invention may contain one or more volatile branched alkanes. The expression "one or more volatile branched alkanes" is intended to mean, without preference, "one or more volatile branched alkane oils".

As volatile branched alkanes, mention may particularly made of $C_5$-$C_{16}$ branched alkanes, such as $C_5$-$C_{16}$ isoalkanes (also known as isoparaffins), isododecane (also known as 2,2,4,4,6-pentamethylheptane), isodecane, isohexadecane, and for example the oils sold under the trade names Isopa by ExxonMobil or Permethyl® by Presperse. Preferably, the volatile hydrocarbon-based oil containing from 8 to 16 carbon atoms is chosen from isododecane, isodecane and isohexadecane, and mixtures thereof, and is in particular isododecane.

The composition according to the invention may contain one or more volatile linear alkanes.

The term "one or more volatile linear alkanes" is intended to mean, without preference, "one or more volatile linear alkane oils".

A volatile linear alkane that is suitable for the invention is liquid at ambient temperature (about 25° C.) and at atmospheric pressure (760 mmHg).

A "volatile linear alkane" that is suitable for the invention is intended to mean a cosmetic linear alkane, which is capable of evaporating on contact with the skin in less than one hour, at ambient temperature (25° C.) and atmospheric pressure (760 mmHg, i.e. 101 325 Pa), which is liquid at ambient temperature, in particular having an evaporation rate ranging from 0.01 to 15 mg/cm²/min, at ambient temperature (25° C.) and atmospheric pressure (760 mmHg).

Preferably, the "volatile linear alkanes" that are suitable for the invention have an evaporation rate ranging from 0.01 to 3.5 mg/cm²/min, at ambient temperature (25° C.) and atmospheric pressure (760 mmHg).

Preferably, the "volatile linear alkanes" that are suitable for the invention have an evaporation rate ranging from 0.01 to 1.5 mg/cm$^2$/min, at ambient temperature (25° C.) and atmospheric pressure (760 mmHg).

More preferably, the "volatile linear alkanes" that are suitable for the invention have an evaporation rate ranging from 0.01 to 0.8 mg/cm$^2$/min, at ambient temperature (25° C.) and atmospheric pressure (760 mmHg).

Even more preferably, the "volatile linear alkanes" that are suitable for the invention have an evaporation rate ranging from 0.01 to 0.3 mg/cm$^2$/min, at ambient temperature (25° C.) and atmospheric pressure (760 mmHg).

Even more preferably, the "volatile linear alkanes" that are suitable for the invention have an evaporation rate ranging from 0.01 to 0.12 mg/cm$^2$/min, at ambient temperature (25° C.) and atmospheric pressure (760 mmHg).

The evaporation rate of a volatile alkane in accordance with the invention (and more generally of a volatile solvent) may in particular be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ which is temperature-regulated (25° C.) and hygrometry-regulated (50% relative humidity).

The liquid is allowed to evaporate freely, without stirring it, while providing ventilation by means of a fan (Papst-Morten, reference 8550 N, rotating at 2700 rpm) placed vertically above the crystallizing dish containing the volatile hydrocarbon-based solvent, the blades being directed towards the crystallizing dish, at a distance of 20 cm relative to the bottom of the crystallizing dish.

The weight of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of the time (in min).

The evaporation rate is then calculated, which corresponds to the tangent to the origin of the curve obtained. The evaporation rates are expressed in mg of volatile solvent evaporated per unit of surface area (cm$^2$) and per unit of time (minute).

According to one preferred embodiment, "the volatile linear alkanes" that are suitable for the invention have a non-zero vapour pressure (also known as saturation vapour pressure), at ambient temperature, in particular a vapour pressure ranging from 0.3 Pa to 6000 Pa.

Preferably, the "volatile linear alkanes" that are suitable for the invention have a vapour pressure ranging from 0.3 to 2000 Pa, at ambient temperature (25° C.).

Preferably, the "volatile linear alkanes" that are suitable for the invention have a vapour pressure ranging from 0.3 to 1000 Pa, at ambient temperature (25° C.).

More preferably, the "volatile linear alkanes" that are suitable for the invention have a vapour pressure ranging from 0.4 to 600 Pa, at ambient temperature (25° C.).

Preferably, the "volatile linear alkanes" that are suitable for the invention have a vapour pressure ranging from 1 to 200 Pa, at ambient temperature (25° C.).

More preferably, the "volatile linear alkanes" that are suitable for the invention have a vapour pressure ranging from 3 to 60 Pa, at ambient temperature (25° C.).

According to one embodiment, a volatile linear alkane that is suitable for use in the invention may have a flash point that is within the range from 30 to 120° C. and more particularly from 40 to 100° C. The flash point is in particular measured according to standard ISO 3679.

According to one embodiment, an alkane that is suitable for use in the invention may be a volatile linear alkane comprising from 8 to 16 carbon atoms.

According to one advantageous embodiment, the "volatile linear alkanes" that are suitable for use in the invention have an evaporation rate, as defined above, ranging from 0.01 to 3.5 mg/cm$^2$/minute, at ambient temperature (25° C.) and atmospheric pressure (760 mmHg), and comprise from 8 to 16 carbon atoms.

A volatile linear alkane that is suitable for the invention may advantageously be of plant origin.

Such an alkane may be obtained, directly or in several steps, from a plant raw material, such as an oil, a butter, a wax, etc.

As examples of alkanes that are suitable for use in the invention, mention may be made of the alkanes described in patent applications by the company Cognis WO 2007/068 371 or WO 2008/155 059 (mixtures of different alkanes differing by at least one carbon). These alkanes are obtained from fatty alcohols, which are themselves obtained from coconut kernel oil or palm oil.

As examples of linear alkanes that are suitable for use in the invention, mention may be made of n-octane (C8), n-nonane (C9), n-decane (C10), n-undecane (C11), n-dodecane (C12), n-tridecane (C13), n-tetradecane (C14), n-hexadecane (C16) and mixtures thereof.

According to a particular embodiment, the volatile linear alkane is chosen from n-nonane, n-undecane, n-dodecane, n-tridecane and n-tetradecane, and mixtures thereof.

The volatile linear alkane may be used alone.

Alternatively or preferentially, a mixture of at least two different volatile linear alkanes, differing from each other by a carbon number n of at least 1, in particular differing from each other by a carbon number of 1 or 2, may be used.

According to a first embodiment, a mixture of at least two different volatile linear alkanes comprising from 10 to 16 carbon atoms and differing from each other by a carbon number of at least 1 may be used. By way of examples, mention may especially be made of the mixtures of volatile linear alkanes C10/C11, C11/C12, and C12/C13.

According to another embodiment, a mixture of at least two different volatile linear alkanes comprising from 10 to 16 carbon atoms and differing from each other by a carbon number of at least 2, is used. By way of examples, mention may in particular be made of the mixtures of volatile linear alkanes C10/C12, and C12/C14, for an even carbon number n and the mixture C11/C13 for an odd carbon number n.

According to one preferred embodiment, a mixture of at least two different volatile linear alkanes comprising from 10 to 16 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes comprising from 8 to 16 carbon atoms and differing from each other by a carbon number of at least 1, also form part of the invention, but mixtures of two volatile linear alkanes according to the invention are preferred (binary mixtures), said two volatile linear alkanes preferably representing more than 95% and better still more than 99% by weight of the total content of volatile linear alkanes in the mixture. According to one particular embodiment of the invention, in a mixture of volatile linear alkanes, the volatile linear alkane having the smallest carbon number is predominant in the mixture.

According to another embodiment of the invention, a mixture of volatile linear alkanes in which the volatile linear alkane having the largest carbon number is predominant in the mixture is used.

As examples of mixtures that are suitable for the invention, mention may be made in particular of the following mixtures:
- from 50% to 90% by weight, preferably from 55% to 80% by weight and more preferentially from 60% to 75% by weight of Cn volatile linear alkane with n ranging from 8 to 16,
- from 10% to 50% by weight, preferably from 20% to 45% by weight and preferably from 24% to 40% by weight of $C_{n+x}$ volatile linear alkane with x greater than or equal to 1, preferably x=1 or x=2, with n+x between 8 and 16, relative to the total weight of the alkanes in said mixture.

In particular, said mixture of alkanes according to the invention contains:
- less than 2% by weight and preferably less than 1% by weight of branched hydrocarbons,
- and/or less than 2% by weight and preferably less than 1% by weight of aromatic hydrocarbons,
- and/or less than 2% by weight, preferably less than 1% by weight and preferentially less than 0.1% by weight of unsaturated hydrocarbons in the mixture.

More particularly, a volatile linear alkane that is suitable for use in the invention may be used in the form of an n-undecane/n-tridecane mixture.

In particular, use will be made of a mixture of volatile linear alkanes comprising:
- from 55% to 80% by weight and preferably from 60% to 75% by weight of a C11 volatile linear alkane (n-undecane),
- from 20% to 45% by weight and preferably from 24% to 40% by weight of a C13 volatile linear alkane (n-tridecane), relative to the total weight of the alkanes in said mixture.

According to one particular embodiment, the mixture of alkanes is an n-undecane/n-tridecane mixture. In particular, such a mixture may be obtained according to Example 1 or Example 2 of WO 2008/155059.

By way of examples of volatile hydrocarbon-based oils that may be used in the invention, mention may be made of:
- n-dodecane, such as that which is sold under the reference Parafol 12-97 by Sasol;
- n-tetradecane, such as that which is sold under the reference Parafol 14-97 by Sasol;
- a mixture of n-dodecane and n-tetradecane;
- isododecane (C12) such as that which is sold by the company Ineos;
- a mixture of $C_{15}$-$C_{16}$ branched alkanes, for example that which is sold by the company SEPPIC under the name Emogreen L15;
- a mixture of $C_{13}$-$C_{15}$ linear and/or branched alkanes, for example that which is sold by the company SEPPIC under the name Emosmart L15.

Volatile oils that may also be used include volatile silicones, such as, for example, volatile linear or cyclic silicone oils, especially those having a viscosity≤8 centistokes ($8\times10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

The various fatty substances as previously defined may be chosen in a varied manner by those skilled in the art so as to prepare a composition having the desired properties, for example in terms of consistency or texture.

According to one particular embodiment of the invention, the fatty phase of the composition comprises at least one oil. Preferably, the composition in accordance with the invention comprises at least one oil chosen from hydrocarbon-based oils and silicone oils. Even more preferentially, the composition in accordance with the invention comprises at least one volatile hydrocarbon-based oil.

According to one embodiment, the composition comprises from 0.5% to 70% by weight of oil(s), relative to the total weight of the composition.

Aqueous Phase

The composition in accordance with the invention comprises at least one aqueous phase. The aqueous phase comprises at least water. According to the galenical form of the composition, the amount of aqueous phase may range from 0.1% to 99% by weight, preferably from 0.5% to 98% by weight, better still from 30 to 95% by weight and even better still from 40 to 95% by weight relative to the total weight of the composition.

The amount of water may represent all or a portion of the aqueous phase and it is generally at least 30% by weight relative to the total weight of the composition, preferably at least 50% by weight, better still at least 60% by weight.

The aqueous phase may comprise at least one organic solvent that is water-miscible at ambient temperature (25° C.), for instance linear or branched monoalcohols containing from 2 to 6 carbon atoms, such as ethanol, propanol, butanol, isopropanol, isobutanol, pentanol or hexanol; polyols especially containing from 2 to 20 carbon atoms, preferably from 2 to 6 carbon atoms, such as glycerine, propylene glycol, isoprene glycol, butylene glycol, pentylene glycol, hexylene glycol, dipropylene glycol, diethylene glycol, triethylene glycol, glycerol, sorbitol, and mixtures thereof.

In a known manner, all the compositions of the invention may comprise one or more of the adjuvants that are common in cosmetics and dermatology: additional surfactants (different than the gemini surfactants as previously described), hydrophilic or lipophilic gelling agents and/or thickeners; moisturizers; emollients; hydrophilic or lipophilic active agents; free-radical scavengers; sequestrants; antioxidants; preservatives; basifying or acidifying agents; fragrances; film-forming agents; fillers; and mixtures thereof.

The amounts of these various adjuvants are those conventionally used in the fields under consideration. In particular, the amounts of active agents vary according to the desired aim and are those conventionally used in the fields under consideration, for example from 0.1 to 20% and preferably from 0.5 to 10% by weight of the total weight of the composition.

When the composition comprises additional surfactants, the latter are preferably present in the composition in a proportion of active material ranging from 0.1% to 30% by weight, and preferably from 0.2% to 20% by weight, relative to the total weight of the composition.

Active Agents

Nonlimiting examples of active agents that may be mentioned include ascorbic acid and derivatives thereof such as 5,6-di-O-dimethylsilyl ascorbate (sold by the company Exsymol under the reference PRO-AA), the potassium salt of dl-alpha-tocopheryl-21-ascorbyl phosphate (sold by the company Senju Pharmaceutical under the reference Sepivital EPC), magnesium ascorbyl phosphate, sodium ascorbyl phosphate (sold by the company Roche under the reference Stay-C 50); phloroglucinol; enzymes; and mixtures thereof.

According to a preferred embodiment of the invention, use is made, among oxidation-sensitive hydrophilic active agents, of ascorbic acid. The ascorbic acid may be of any nature. Thus, it may be of natural origin in powder form or in the form of orange juice, preferably orange juice concentrate. It may also be of synthetic origin, preferably in powder form.

As other active agents that may be used in the composition of the invention, examples that may be mentioned include moisturizers, such as protein hydrolysates and polyols, for instance glycerol, glycols, for instance polyethylene glycols; natural extracts; anti-inflammatories; oligomeric proanthocyanidins; vitamins such as vitamin A (retinol), vitamin E (tocopherol), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxydiphenyl ether (or triclosan), 3,4,4'-trichlorocarbanilide (or triclocarban) and the acids indicated above, and especially salicylic acid and derivatives thereof; mattifying agents, for instance fibres; tensioning agents; and mixtures thereof.

Needless to say, those skilled in the art will take care to select the optional adjuvant(s) added to the composition according to the invention such that the advantageous properties intrinsically associated with the composition in accordance with the invention are not, or are not substantially, adversely affected by the envisioned addition.

The compositions in accordance with the invention may for example be in the form of a cream, a milk, or a fluid product that can be sprayed.

The compositions according to the invention may in particular be in the form of a vaporizable emulsion applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are in particular described in U.S. Pat. Nos. 4,077,441 and 4,850,517.

The compositions in accordance with the invention that are packaged in aerosols in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition. The compositions may also be impregnated onto supports such as wipes, or they may be packaged as lotions in a bottle with a reducing agent.

The examples that follow will allow the invention to be understood more clearly, without, however, being limiting in nature. The amounts indicated are weight percentages of raw materials, unless otherwise mentioned. The names of the compounds are given as the chemical or INCI names.

EXAMPLES

Example of Lipophilic Polymer Synthesis

Determination of the Molecular Weight by Gel Permeation Chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes in order to assist with the dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 µm nylon filter, before being injected into the liquid chromatograph. The standard used for the calibration are the Easi Vial narrow polystyrene (PS) standards from Agilent Technologies.

Polystyrene standards ranging from 2 520 000 to 162 Daltons were used for the calibration.

The system is equipped with a PSS SECcurity 1260 RI detector. The polystyrene calibration curve was used to determine the average molecular weight. The recording of the diagrams and the determination of the various molecular weights was carried out by the Win GPC Unichrom 81 program.

Determination of the Melting Point by Differential Scanning Calorimetry (or DSC):

This method describes the general procedure for determining the melting point of polymers by differential scanning calorimetry. This method is based on the standards ASTM E791 and ASTM D 34182 and the DSC calibration is carried out according to the standard ASTM E 9672.

Behenyl Acrylate/2-Hydroxyethyl Acrylate Copolymer (Polymer 1):

In a 4-necked flask equipped with side-blade mixer, an internal thermometer, two funnels, a reflux condenser, and an extension for two other necks, 175 g of behenyl acrylate, 25 g of 2-hydroxyethyl acrylate and 0.4 g of 2,2'-azobis(2-methylbutyronitrile) (AkzoNobel) were added, over the course of 60 minutes at 80° C., to 40 g of isopropanol, with stirring, after having removed the oxygen from the system by means of a nitrogen flush for 20 minutes.

The mixture was stirred at 80° C. for 3 hours. The solvent was then eliminated by vacuum distillation, then 1 g of dilauryl peroxide was added and the reaction was continued for 60 minutes at 110° C. The step was repeated. The mixture was then cooled to 90° C. and a jet of demineralized water was added, then the mixture was stirred. The water was eliminated by vacuum distillation.

Molecular weight: Mn=7300 g/mol, Mw=21000, Mw/Mn=2.8

Melting point: 65° C.

Formulation Examples

The compositions described in the examples below were prepared according to the following procedure:

1—Prepare the oily phase by introducing the screening agents into said oily phase.

Dissolve the screening agents by heating to 70° C., add the fatty-phase structuring polymer and heat until the polymer has completely dissolved.

2—Prepare the aqueous phase and add the gemini surfactant, heat the phase to the same temperature as the fatty phase.

3—Emulsify the two phases together using a mixer of rotor/stator type at 70° C., then cool to 30° C., and add the thickeners and the alcohol.

For each composition, the viscosity was measured, then the sensory aspect was evaluated during and after application thereof to the skin; the in vitro SPF value was also measured.

Viscosity Measurement

The viscosity measurement is generally performed at 25° C., using a Rheomat RM180® viscometer equipped with a No. 2 or 3 spindle, the measurement being performed after 10 minutes of rotation of the spindle in the composition (after which time stabilization of the viscosity is observed) at a shear rate of 200 $s^{-1}$.

Protocol for Evaluating the Tack and the Greasiness

The tack is evaluated by a panel of sensory experts made up of 5 individuals. Each composition is applied to the forearm at a dose of 2 mg/cm². The product was spread by circular movements until it had penetrated (approximately 30 seconds). The tack is evaluated after 2 minutes of drying, by applying the back of the hand to the treated area, according to scale ranging from 1 to 15 in which 1 constitutes a reference that is not very tacky or not very greasy and 15 constitutes a reference that is very tacky or very greasy.

In Vitro SPF

The sun protection factor (SPF) is determined according to the "in vitro" method described by B. L. Diffey in J. Soc. Cosmet. Chem. 40, 127-133, (1989). The measurements were taken by means of a UV-2000 spectrophotometer from the company Labsphere. Each composition is applied to a rough plate of PMMA, in the form of a uniform and even deposit in a proportion of 1.3 mg/cm².

Example 1 According to the Invention: Composition in the Form of a Direct Emulsion The following composition was prepared:

|  | Composition A (invention) |
|---|---|
| OCTOCRYLENE (UVINUL N539 from BASF) | 7.00 |
| ETHYLHEXYL SALICYLATE (NEO HELIOPAN OS/H from SYMRISE) | 5.00 |
| BUTYL METHOXYDIBENZOYLMETHANE (CHEM 1789 from EMSPEC CHEMICALS) | 3.00 |
| ISONONYL ISONONANOATE (DUB ININ from STEARINERIES DUBOIS) | 4.00 |
| DISODIUM ETHYLENEDIAMINE TETRAACETATE DIHYDRATE | 0.1 |
| POLYDIMETHYLSILOXANE (VISCOSITY: 5 cSt) | 2.5 |
| ALPHA-OMEGA DIHYDROXYL POLYDIMETHYLSILOXANE/POLYDIMETHYLSILOXANE MIXTURE 5 CST | 2 |
| GLYCEROL | 7.00 |
| XANTHAN GUM | 0.25 |
| ETHOXYLATED (15 EO) SODIUM ETHYLDIAMIDO-N-COCOYL SULFONATE/BEHENYL ALCOHOL/GLYCERYL STEARATE/CITRATE MIXTURE (CERALUTION H from SASOL) | 3.5 |
| POLYACRYLAMIDOMETHYLPROPANESULFONIC ACID PARTIALLY NEUTRALIZED WITH AQUEOUS AMMONIA AND HIGHLY CROSSLINKED | 0.5 |
| Polymer 1 as previously synthesized | 2 |
| PRESERVATIVE(S) | 1 |
| WATER | qs 100 |

The composition A in accordance with the present invention has good sun protection factor, while at the same time having good cosmetic properties, such as anon-greasy and non-tacky feel, while at the same time being stable, in particular from the physicochemical viewpoint.

Comparative Example 2: Compositions in the Form of Direct Emulsions

The following compositions are prepared.

|  | Composition B (invention) | Composition C (invention) | Composition D (comparative) |
|---|---|---|---|
| BIS-ETHYLHEXYLOXYPHENOL METHOXYPHENYL TRIAZINE (TINOSORB S from BASF) | 4.50 | 4.50 | 4.50 |
| ETHYLHEXYL SALICYLATE (NEO HELIOPAN OS/H from SYMRISE) | 5.00 | 5.00 | 5.00 |
| DIETHYLAMINO HYDROXYBENZOYL HEXYL BENZOATE (UVINUL A PLUS GRANULAR from BASF) | 5.50 | 5.50 | 5.50 |
| ETHYLHEXYL TRIAZONE (UVINUL T 150 from BASF) | 3.50 | 3.50 | 3.50 |
| DICAPRYLYL CARBONATE | 10.00 | 10.00 | 10.00 |
| DIISOPROPYL SEBACATE | 7.00 | 7.00 | 7.00 |
| CAPRYLIC/CAPRIC TRIGLYCERIDE | 5.00 | 5.00 | 5.00 |
| DEXTRIN PALMITATE | 2.00 | 2.00 | 2.00 |
| ETHOXYLATED (15 EO) SODIUM ETHYLDIAMIDO-N-COCOYL SULFONATE/BEHENYL ALCOHOL/GLYCERYL STEARATE/CITRATE MIXTURE (CERALUTION H from SASOL) | 3.00 | 2.00 | — |
| STEARIC ACID | — | — | 1.50 |
| GLYCERYL MONO/DISTEARATE/POLYETHYLENE GLYCOL STEARATE (100 EO) MIXTURE (50/50) (ARLACEL 165 from CRODA) | — | — | 1.50 |
| Polymer 1 as previously synthesized | 2.00 | 3.00 | 2.00 |
| GLYCEROL | 3.00 | 3.00 | 3.00 |
| pH ADJUSTER(S) | 0.5 | 0.5 | 0.5 |
| PROPANEDIOL | 3.00 | 3.00 | 3.00 |
| PRESERVATIVE(S) | 0.50 | 0.50 | 0.50 |
| LIGHTLY CROSSLINKED | 1.50 | 1.50 | 1.50 |

-continued

|  | Composition | | |
|---|---|---|---|
|  | B (invention) | C (invention) | D (comparative) |
| ACRYLIC POLYMER IN EMULSION, in solution at 30% in water (CARBOPOL AQUA SF-1 from LUBRIZOL) | | | |
| DENAT. ALCOHOL | 5.00 | 5.00 | 5.00 |
| WATER | qs 100 | qs 100 | qs 100 |

The following results were obtained.

|  | Composition | | |
|---|---|---|---|
|  | B (invention) | C (invention) | D (comparative) |
| Viscosity (Pa · s) at 24 h | 1.23 | 1.17 | 0.94 |
| Non-tacky finish (Score by sensory expert panel, out of 15; 1 = not very tacky; 15 = very tacky) | 4.7 ± 0.2 | 4.1 ± 0.8 | 7.2 ± 1.8 |
| Non-greasy finish (Score by sensory expert panel, out of 15; 1 = not very greasy; 15 = very greasy) | 4.1 ± 0.2 | 4.4 ± 0.6 | 6.6 ± 1.0 |
| in vitro SPF | 79.1 ± 5.6 | 80.9 ± 6.1 | 58.9 ± 5.9 |

These results show that the compositions B and C according to the invention comprising a gemini surfactant (Ceralution H from Sasol) make it possible to obtain a better sun protection factor than the composition D according to the prior art comprising a surfactant which is not a gemini surfactant and the same UV-screening agent at the same concentration, at the same time having a less tacky and less greasy skin finish.

Comparative Example 3: Compositions in the Form of Direct Emulsions

The following compositions were prepared.

|  | Composition | |
|---|---|---|
|  | E (invention) | F (comparative) |
| BUTYL METHOXYDIBENZOYLMETHANE (EUSOLEX 9020 from MERCK) | 3.00 | 3.00 |
| ETHYLHEXYL SALICYLATE (NEO HELIOPAN OS/H from SYMRISE) | 5.00 | 5.00 |
| ETHYLHEXYL TRIAZONE (UVINUL T 150 from BASF) | 2.50 | 2.50 |
| TEREPHTHALYLIDENE DICAMPHOR SULFONIC ACID (MEXORYL SX from CHIMEX) | 0.9 | 0.9 |
| DROMETRIZOLE TRISILOXANE (SILATRIZOLE from RHODIA) | 3.00 | 3.00 |
| BIS-ETHYLHEXYLOXYPHENOL METHOXYPHENYL TRIAZINE (TINOSORB S from BASF) | 5.00 | 5.00 |
| DISODIUM ETHYLENEDIAMINETETRAACETATE DIHYDRATE | 0.1 | 0.1 |
| pH ADJUSTER(S) | 0.41 | 0.41 |
| DIISOPROPYL SEBACATE | 8.00 | 8.00 |

|  | Composition | |
|---|---|---|
|  | E (invention) | F (comparative) |
| ISOPROPYL N-LAUROYL SARCOSINATE | 1.00 | 1.00 |
| ETHOXYLATED (15 EO) SODIUM ETHYLDIAMIDO-N-COCOYL SULFONATE/BEHENYL ALCOHOL/ GLYCERYL STEARATE/CITRATE MIXTURE (CERALUTION H from SASOL) | 2.00 | 2.00 |
| LIGHTLY CROSSLINKED ACRYLIC POLYMER IN EMULSION, in solution at 30% in water (CARBOPOL AQUA SF-1 from LUBRIZOL) | 2.00 | 2.00 |
| Polymer 1 as previously synthesized | 3.00 | — |
| POLY C10-30 ALKYL ACRYLATE (INTELIMER IPA 13-1 NG from AIR PRODUCTS AND CHEMICALS) | — | 3.00 |
| DENAT. ALCOHOL | 10.00 | 10.00 |
| GLYCEROL | 6.00 | 6.00 |
| PRESERVATIVE(S) | 0.50 | 0.50 |
| Water | qs 100 | qs 100 |

The following results were obtained.

|  | Composition | |
|---|---|---|
|  | E (invention) | F (comparative) |
| Viscosity (Pa · s) at 24 h | 0.12 | 0.15 |
| Non-tacky finish (Score by sensory expert panel, out of 15; 1 = not very tacky; 15 = very tacky) | 2.6 ± 1.5 | 6.3 ± 0.3 |
| in vitro SPF | 62.7 ± 1.5 | 50.1 ± 2.8 |

These results show that the composition E comprising a lipophilic polymer according to the invention (Polymer 1) makes it possible to obtain an in vitro SPF value much higher than that which is obtained with the composition F according to the prior art comprising another lipophilic polymer (Interlimer IPA 13-1 NG from Air Products and Chemicals) and the same UV-screening agent, at the same concentration, while at the same time having a less tacky skin finish.

The invention claimed is:
1. A composition in the form of an emulsion comprising 0.1% to 45% by weight based upon the weight of the composition of at least one UV-screening agent, 0.01% to 5% by weight based upon the weight of the composition of at least one gemini surfactant having the Chemical Formula (II) shown below, or stereoisomers thereof:

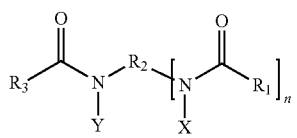

in which:
$R_1$ and $R_3$ denote, independently of each other, an alkyl radical containing from 1 to 25 carbon atoms;
$R_2$ denotes a spacer constituted of a linear or branched alkylene chain containing from 1 to 12 carbon atoms;

X and Y denote, independently of each other, $-(C_2H_4O)_a-(C_3H_6O)_b Z$, in which Z denotes a hydrogen atom or a radical $-CH_2-COOM$, $-SO_3M$, $-P(O)(OM)_2$, $-C_2H_4-SO_3M$, $-C_3H_6-SO_3M$ or $-CH_2(CHOH)_4CH_2OH$, where M represents H or an alkali metal or alkaline-earth metal or ammonium or alkanolammonium ion, a ranges from 0 to 15, b ranges from 0 to 10, and the sum of a +b ranges from 1 to 25; and n ranges from 1 to 10;

and 0.1% to 10% by weight based upon the weight of the composition of at least one lipophilic polymer chosen from copolymers of behenyl acrylate and 2-hydroxyethyl acrylate having a number-average molecular weight Mn ranging from 5000 to 9000 g/mol and a weight ratio of the 2-hydroxyethyl acrylate to behenyl acrylate from 1:15 to 1:1; and wherein the sum of the total units of the 2-hydroxyethyl acrylate and behenyl acrylate is 100% by weight of the total weight of the copolymer.

2. The composition according to claim 1, in which, for the at least one gemini surfactant of formula (II), each of the $R_1-CO-$ and $R_3-CO-$ groups is a residue from a fatty acid that comprises from 8 to 20 carbon atoms.

3. The composition according to claim 1, in which, for the at least one gemini surfactant of formula (II), each of the $R_1-CO-$ and $R_3-CO-$ groups denotes a coconut fatty acid residue.

4. The composition according to claim 1, in which, for the at least one gemini surfactant of formula (II), for each of the X and Y radicals, the sum of a and b has a mean value ranging from 10 to 20.

5. The composition according to claim 1, in which, for the at least one gemini surfactant of formula (II), Z is the $-SO_3M$ group, where M is an alkali metal ion.

6. The composition according to claim 1, in which, for the at least one gemini surfactant of formula (II), n is equal to 1.

7. The composition according to claim 1, in which the at least one gemini surfactant of formula (II) has the following structure:

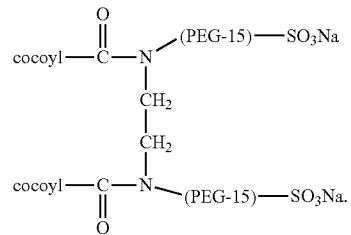

8. The composition according to claim 1, in which the at least one gemini surfactant of formula (II) is mixed with (a) a glyceryl ester of a $C_6$-$C_{22}$ fatty acid, (b) a diester of a $C_6$-$C_{22}$ fatty acid and of citric acid and of glycerol, and (c) a $C_{10}$-$C_{30}$ fatty alcohol.

9. The composition according to claim 1, in which the at least one lipophilic polymer has a melting point ranging from 60° C. to 69° C.

10. The composition according to claim 9 in which the at least one gemini surfactant of formula (II) has the following structure:

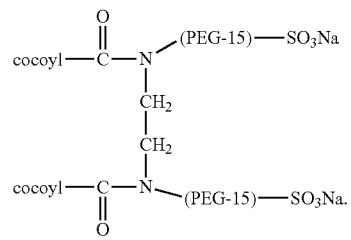

11. The composition according to claim 1, in which the at least one lipophilic polymer is present in an amount ranging from 0.1% to 3% by weight relative to the total weight of the composition.

12. A process for caring for and/or removing makeup from and/or cleansing keratin materials which comprises applying to the keratin materials the composition according to claim 1.

13. A cosmetic process for treating a keratin material, in which the composition as defined in claim 1 is applied to the keratin material.

14. The composition according to claim 1, which is an oil-in-water emulsion.

* * * * *